(12) United States Patent
Saitoh et al.

(10) Patent No.: US 7,932,592 B2
(45) Date of Patent: Apr. 26, 2011

(54) COMPOUND AND ORGANIC LIGHT-EMITTING ELEMENT

(75) Inventors: Akihito Saitoh, Yokohama (JP); Keiji Okinaka, Kawasaki (JP); Satoshi Igawa, Fujisawa (JP); Naoki Yamada, Tokyo (JP); Chika Negishi, Yokosuka (JP); Takao Takiguchi, Tokyo (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 805 days.

(21) Appl. No.: 11/736,628

(22) Filed: Apr. 18, 2007

(65) Prior Publication Data

US 2008/0124577 A1 May 29, 2008

(30) Foreign Application Priority Data

Apr. 24, 2006 (JP) ................. 2006-119358
Feb. 22, 2007 (JP) ................. 2007-042664

(51) Int. Cl.
*H01L 51/54* (2006.01)
*C09K 11/06* (2006.01)

(52) U.S. Cl. ........ 257/690; 428/917; 313/504; 313/506; 252/301.16; 257/40; 257/103; 585/400

(58) Field of Classification Search .................. None
See application file for complete search history.

(56) References Cited

U.S. PATENT DOCUMENTS

| | | | |
|---|---|---|---|
| 7,129,386 B2 | 10/2006 | Saitoh et al. | 585/26 |
| 7,173,131 B2 | 2/2007 | Saitoh et al. | 544/336 |
| 2003/0044643 A1* | 3/2003 | Arakane et al. | 428/690 |
| 2005/0236974 A1 | 10/2005 | Suzuki et al. | 313/504 |
| 2005/0236977 A1 | 10/2005 | Yamada et al. | 313/504 |
| 2006/0068221 A1 | 3/2006 | Saitoh et al. | 428/690 |
| 2006/0115678 A1 | 6/2006 | Saitoh et al. | 428/690 |
| 2006/0255723 A1 | 11/2006 | Saitoh et al. | 313/504 |
| 2007/0085473 A1 | 4/2007 | Moriyama et al. | 313/504 |
| 2007/0207346 A1 | 9/2007 | Saitoh et al. | 428/690 |
| 2007/0232841 A1 | 10/2007 | Igawa et al. | 585/27 |

FOREIGN PATENT DOCUMENTS

| | | |
|---|---|---|
| JP | 10-189248 | 7/1998 |
| JP | 2002-069044 | 3/2002 |
| JP | 2003-347056 | 12/2003 |
| WO | WO 2004/020371 A1 * | 3/2004 |

* cited by examiner

*Primary Examiner* — Callie E Shosho
*Assistant Examiner* — Michael H Wilson
(74) *Attorney, Agent, or Firm* — Fitzpatrick, Cella, Harper & Scinto

(57) ABSTRACT

A novel organic compound and a high-performance organic light-emitting element containing the same. The organic light-emitting element contains a novel compound represented by general formula (1):

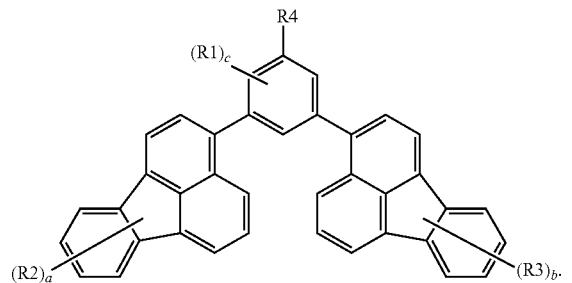

(1)

5 Claims, 1 Drawing Sheet

FIGURE
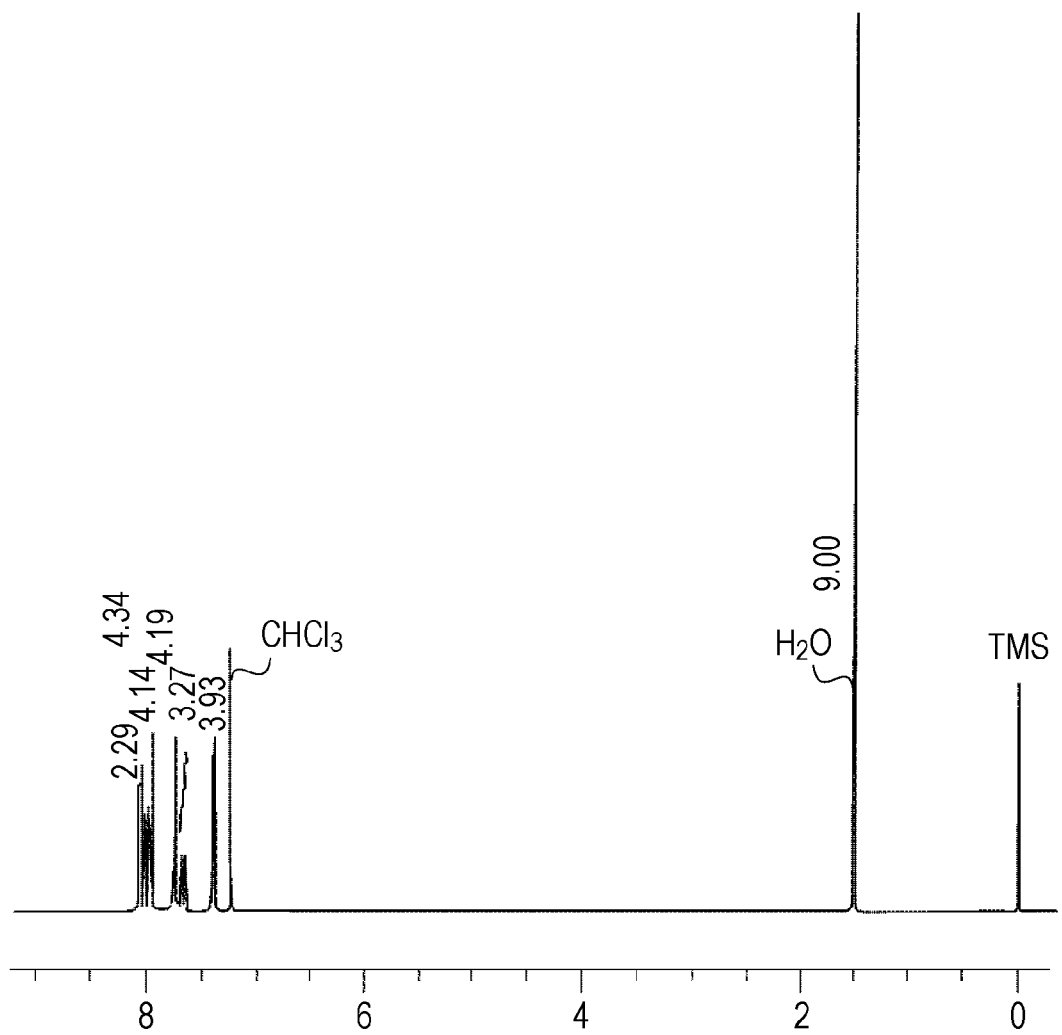

COMPOUND AND ORGANIC LIGHT-EMITTING ELEMENT

BACKGROUND OF THE INVENTION

1. Field of the Invention

The present invention relates to a novel compound and a light-emitting element using the same.

2. Description of the Related Art

Recent advances in organic light-emitting elements have been remarkable. Thin and lightweight light-emitting devices have been developed that are characterized by a high luminance at a low applied voltage, a wide choice of color, and high-speed response. Accordingly, a wide range of applications of the organic light-emitting element may be expected.

Fluoranthene compounds have been disclosed in Japanese Patent Laid-Open Nos. 10-189248, 2002-69044, and 2003-347056.

However, there are still many problems with organic light-emitting elements, including lack of durability, characterized by changes in performance after long term use and excess degradation thereof, caused, for example, by an oxygen-containing gas and/or moisture.

When a light-emitting element is to be applied to a full-color display and the like, it is desired that the light emission of blue, green, and red have a longer life, that a high conversion efficiency is realized, and that superior color purity is obtained.

SUMMARY OF THE INVENTION

The present invention provides a compound used for a light-emitting element, the compound exhibiting a light emission color with significantly high purity and having highly efficient, highly luminant, and long-lived light emission.

In addition, the present invention provides an organic light-emitting element that can be easily manufactured and that can be formed at a relatively low cost.

The present invention provides a compound represented by the following general formula (1).

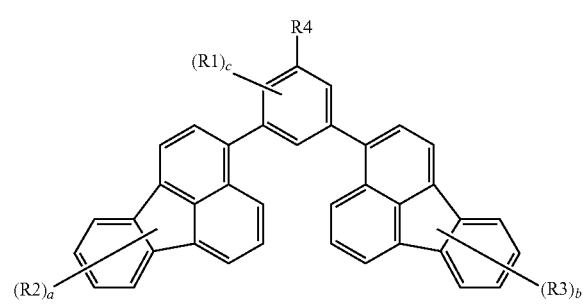

(1)

In the above general formula (1), R4 represents a substituted or an unsubstituted alkyl group.

R1 to R3 each independently represent a hydrogen atom, a halogen atom, a cyano group, an alkyl group, an alkoxy group, a silyl group, an amino group, an aryl group, or a heterocyclic group.

The alkyl group, the alkoxy group, the silyl group, the amino group, the aryl group, and the heterocyclic group may include at least one substituent.

R1, R2, and R3 are the same or different from each other.

A plurality of R1 may bond to each other to form a ring, a plurality of R2 may bond to each other to form a ring, and a plurality of R3 may bond to each other to form a ring.

In addition, c is an integer from 1 to 3, and a and b are each independently an integer from 1 to 9.

The compound of the present invention has a high glass transition temperature. In addition, when the compound of the present invention is present as a host or a guest of a light-emitting layer, highly efficient light emission can be realized. The organic light-emitting element of the present invention has high heat stability and superior durability besides highly efficient light emission at a low applied voltage.

Further features of the present invention will become apparent from the following description of exemplary embodiments with reference to the attached drawings.

BRIEF DESCRIPTION OF THE DRAWINGS

The FIGURE is a view showing a $^1$H-NMR (CDCl$_3$) spectrum of an exemplified compound A-2 according to the present invention.

DESCRIPTION OF THE EMBODIMENTS

The compound of the present invention is a compound represented by the following general formula (1).
1) c
In the above general formula (1), R4 represents a substituted or an unsubstituted alkyl group.

R1 to R3 each independently represent a hydrogen ato$^a$ a halogen atom, a cyan$^b$ group, an alkyl group, an alkoxy group, a silyl group, an amino group, an aryl group, or a heterocyclic group.

The alkyl group, the alkoxy group, the silyl group, the amino group, the aryl group, and the heterocyclic group may include at least one substituent.

R1, R2, and R3 are the same or different from each other.

A plurality of R1 groups may bond to each other to form a ring, and a plurality of R2 groups may likewise bond to each other to form a ring. A plurality of R3 groups may likewise bond to form a ring.

In addition, c is an integer from 1 to 3, and a and b are each independently an integer from 1 to 9.

The hydrogen atom may be replaced with a deuterium atom.

The halogen atom may be fluorine, chlorine, bromine, or iodine.

As the alkyl group, for example, there may be mentioned a methyl group, methyl-d1 group, methyl-d3 group, ethyl group, ethyl-d5 group, n-propyl group, n-butyl group, n-pentyl group, n-hexyl group, n-heptyl group, n-octyl group, n-decyl group, iso-propyl group, iso-propyl-d7 group, iso-butyl group, sec-butyl group, tert-butyl group, tert-butyl-d9 group, iso-pentyl group, neopentyl group, tert-octyl group, fluoromethyl group, difluoromethyl group, trifluoromethyl group, 2-fluoroethyl group, 2,2,2-trifluoroethyl group, perfluoroethyl group, 3-fluoropropyl group, perfluoropropyl group, 4-fluorobutyl group, perfluorobutyl group, 5-fluoropentyl group, 6-fluorohexyl group, chloromethyl group, trichloromethyl group, 2-chloroethyl group, 2,2,2-trichloroethyl group, 4-chlorobutyl group, 5-chloropentyl group, 6-chlorohexyl group, bromomethyl group, 2-bromoethyl group, iodomethyl group, 2-iodoethyl group, hydroxymethyl group, hydroxyethyl group, cyclopropyl group, cyclobutyl group, cyclopentyl group, cyclohexyl group, cyclopentylmethyl group, cyclohexylmethyl group, cyclohexylethyl group, 4-fluorocyclohexyl group, norbornyl group, and adamantyl group.

As the alkoxy group, for example, there may be mentioned an alkyloxy group, an aralkyloxy group, and an aryloxy group having the above substituted or unsubstituted aryl group or heterocyclic group. More particularly, for example, as the alkoxy group, a methoxy group, ethoxy group, propoxy group, 2-ethyl-octyloxy group, phenoxy group, 4-tert-butylphenoxy group, benzyloxy group, and thienyloxy group may be mentioned.

As the silyl group, for example, a trimethylsilyl group, triethylsilyl group, tert-butyldimethylsilyl group, iso-propyldimethylsilyl group, triphenylsilyl group, phenyldimethylsilyl group, mesityldimethylsilyl group, and dimesitylmethylsilyl group may be mentioned.

In the amino group (—NR'R"), R' and R" are each independently selected from a hydrogen atom, deuterium atom, alkyl group, aralkyl group, aryl group, heterocyclic group, arylene group, alkyl groups connected by a divalent heterocyclic group, alkenyl group, alkynyl group, amino group, silyl group, ether group, thioether group, and carbonyl group.

The substituent R' and R" groups may further have at least one of the formula.

The amino group of the formula (—NR'R") may be an amino group, N-methyl amino group, N-ethyl amino group, N,N-dimethyl amino group, N,N-diethylamino group, N-methyl-N-ethylamino group, N-benzylamino group, N-methyl-N-benzylamino group, N,N-dibenzylamino group, anilino group, N,N-diphenylamino group, N-phenyl-N-tolylamino group, N,N-ditolylamino group, N-methyl-N-phenylamino group, N,N-dianisolylamino group, N-mesityl-N-phenylamino group, N,N-dimesitylamino group, N-phenyl-N-(4-tert-butylphenyl)amino group, and N-phenyl-N-(4-trifluoromethylphenyl)amino group.

The aryl groups represented by R1 may be, for example, a phenyl group, phenyl-d5 group, 4-methylphenyl group, 4-methoxyphenyl group, 4-ethylphenyl group, 4-fluorophenyl group, 4-trifluorophenyl group, 3,5-dimethylphenyl group, 2,6-diethylphenyl group, mesityl group, 4-tert-butylphenyl group, ditolylaminophenyl group, biphenyl group, terphenyl group, naphthyl group, naphthyl-d7 group, acenaphthylenyl group, anthryl group, anthryl-d9 group, phenanthryl group, phenanthryl-d9 group, pyrenyl group, pyrenyl-d9 group, acephenanthrylenyl group, aceanthrylenyl group, chrycenyl group, dibenzochrycenyl group, benzoanthryl group, benzoanthryl-d11 group, dibenzoanthryl group, naphthacenyl group, picenyl group, pentacenyl group, fluorenyl group, triphenylenyl group, perylenyl group, and perylenyl-d11 group.

As aryl groups represented by R2 and R3, for example, there may be mentioned a phenyl group, phenyl-d5 group, 4-methylphenyl group, 4-methoxyphenyl group, 4-ethylphenyl group, 4-fluorophenyl group, 4-trifluorophenyl group, 3,5-dimethylphenyl group, 2,6-diethylphenyl group, mesityl group, 4-tert-butylphenyl group, ditolylaminophenyl group, biphenyl group, terphenyl group, naphthyl group, naphthyl-d7 group, acenaphthylenyl group, anthryl group, anthryl-d9 group, phenanthryl group, phenanthryl-d9 group, pyrenyl group, pyrenyl-d9 group, acephenanthrylenyl group, aceanthrylenyl group, chrycenyl group, dibenzochrycenyl group, benzoanthryl group, benzoanthryl-d11 group, dibenzoanthryl group, naphthacenyl group, picenyl group, pentacenyl group, fluorenyl group, triphenylenyl group, perylenyl group, and perylenyl-d11 group.

As the heterocyclic group, for example, there may be mentioned a pyrrolyl group, pyridyl group, pyridyl-d5 group, bipyridyl group, methylpyridyl group, pyrimidinyl group, pyrazinyl group, pyridazinyl group, terpyrrolyl group, thienyl group, thienyl-d4 group, terthienyl group, propylthienyl group, benzothienyl group, dibenzothienyl group, dibenzothienyl-d7 group, furyl group, furyl-d4 group, benzofuryl group, isobenzofuryl group, dibenzofuryl group, dibenzofuryl-d7 group, quinolyl group, quinolyl-d6 group, isoquinolyl group, quinoxalinyl group, naphthylidinyl group, quinazolinyl group, phenanthridinyl group, indolizinyl group, phenazinyl group, carbazolyl group, oxazolyl group, oxadiazolyl group, thiazolyl group, thiadiazolyl group, acrydinyl group, and phenazinyl group.

The substituents for the above alkyl group, alkoxy group, silyl group, amino group, aryl group, and heterocyclic group include alkyl groups such as a methyl group, ethyl group, and propyl group; aryl groups such as a phenyl group, biphenyl group, naphthyl group, and fluoranthenyl group; heterocyclic groups such as a thienyl group, pyrrolyl group, and pyridyl group; amino groups such as a dimethylamino group, diethylamino group, dibenzylamino group, diphenylamino group, ditolylamino group, and dianisolylamino group; alkoxy groups such as a methoxy group and ethoxy group; halogen atoms such as fluorine, chlorine, bromine, and iodine; a hydroxyl group; a cyano group; and a nitro group.

The compound of the present invention is a compound in which two meta-positions of a benzene ring are each substituted with a 3-fluoranthenyl group. This structure can be easily synthesized.

In addition, the inventors of the present invention found that when this compound is used particularly as a guest material of a light-emitting layer of an organic light-emitting element, various beneficial properties, such as highly efficient light emission, stable high luminance for a long period of time, and a small degradation in quality caused by current application, can be obtained. The guest material is an accessory component of the light-emitting layer, and the primary component is called a host material.

It is believed that one of the reasons for the above enhanced properties is that since repulsion of the peri-position, that is, the 4-position, of each fluoranthene ring occurs, the fluoranthene rings are each distorted with respect to the plane of the benzene ring.

In particular, it is believed that when the compound of the present invention is used as a guest material, aggregation is not likely to occur in the light-emitting layer, and, as a result, concentration quenching can be suppressed.

When the compound of the present invention is used as a guest material, the concentration of the guest material to the host material is set in the range of 0.01 to 80 percent by weight and is preferably set in the range of 1 to 40 percent by weight. In addition, the guest material may be uniformly contained in a layer made of the host material or may be contained in the host material in a concentration gradient. Alternatively, the guest material may be used in a layer having a first region which includes the guest material and a second region which contains the host material and no guest material.

In addition, the compound of the present invention has a preferable glass transition temperature, and hence an organic EL element having high durability can be expected. The reason for this is that the molecular weight of the compound of the present invention is preferably 500 or more.

In the compound used in the present invention, since two 3-fluoranthenyl groups are substituted at the meta-positions of a benzene ring, the bandgap is increased, and hence a more preferable blue light emission can be observed.

The reason for this is that the spread of a conjugated system can be suppressed as compared to a compound in which two 3-fluoranthenyl groups are substituted at the para-positions of a benzene ring.

Furthermore, when a substituent is introduced into the fluoranthenyl group of the compound according to the present invention so as to increase the distortion between the plane of the fluoranthenyl group and the plane of the benzene ring, adjustment of the bandgap can be further performed to enhance color purity.

In addition, the compound of the present invention has high solubility in organic solvents such as benzene, toluene or the like. In particular, when the benzene ring has an alkyl group, the solubility is further improved. The compound as described above is preferably used since the purity thereof can be increased in a purification process, in particular, in a column purification process.

Among alkyl groups, a tert-butyl group has a significant effect of improving solubility. Furthermore, in an organic light-emitting element, the above alkyl group suppresses aggregation between molecules, and when a tert-butyl group is employed in the inventive compounds, and the resulting compound as a light-emitting material, it is effective in suppressing concentration quenching.

Hereinafter, examples of the compound according to the present invention will be shown.

Compound Group A

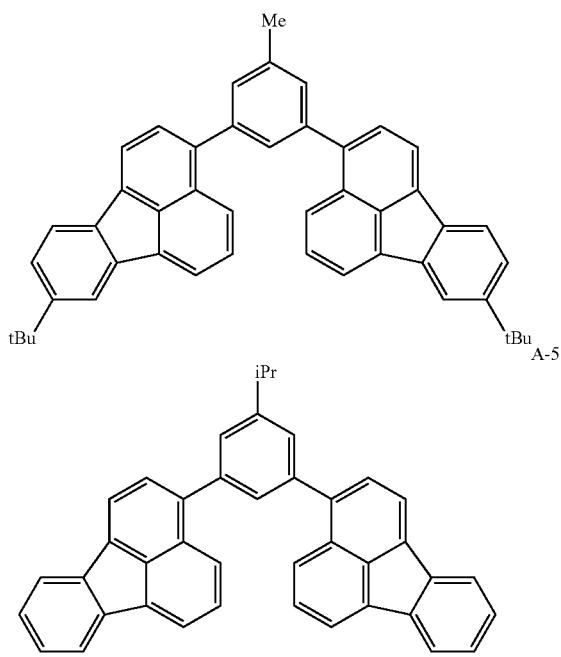

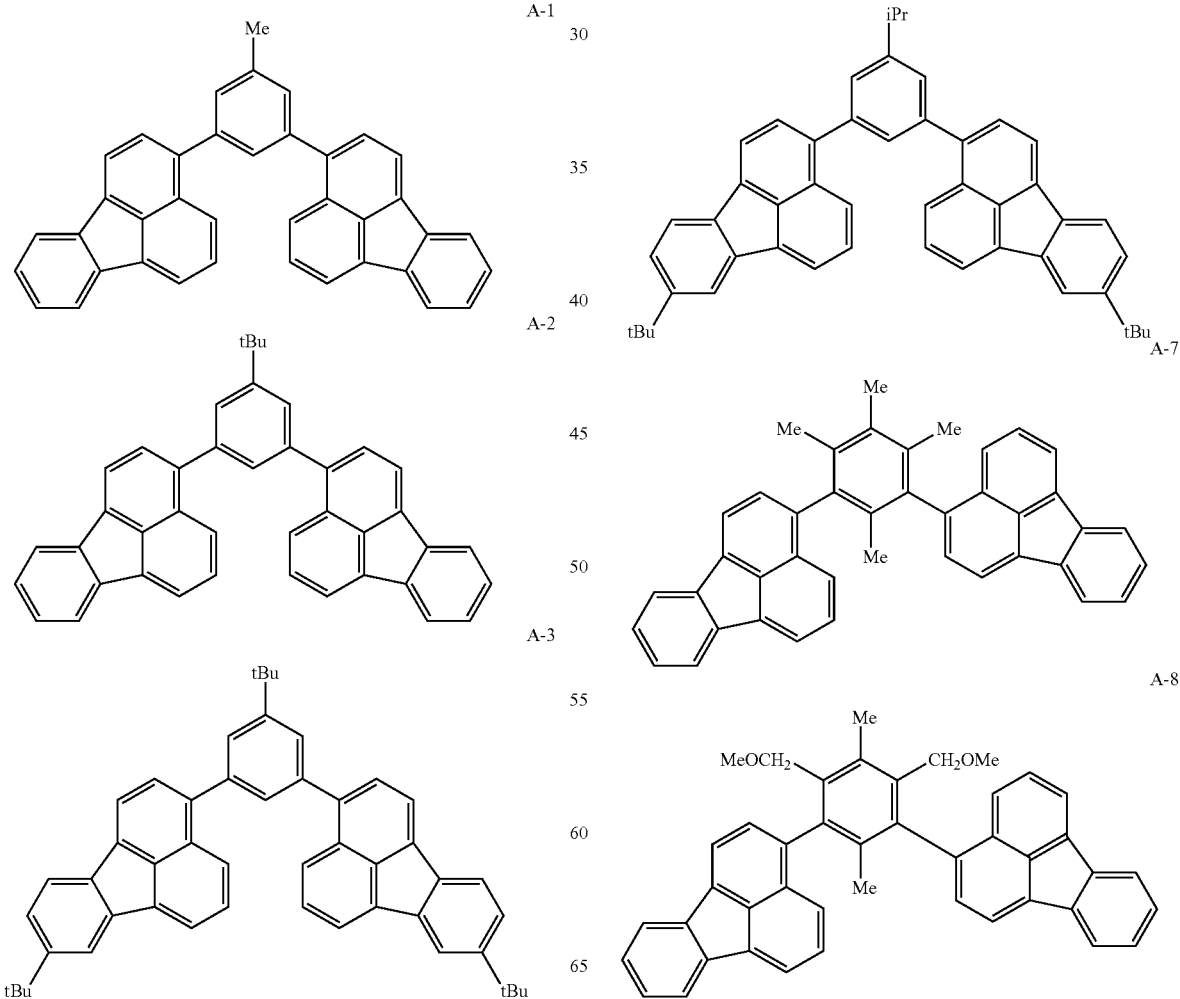

A-9
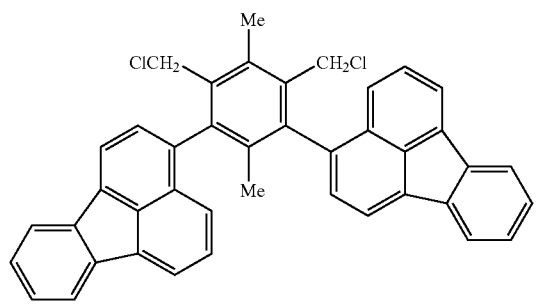
A-10
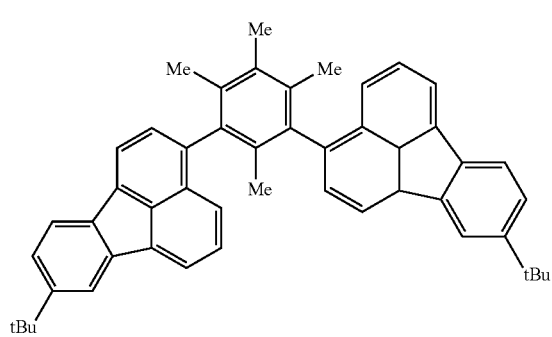
A-11
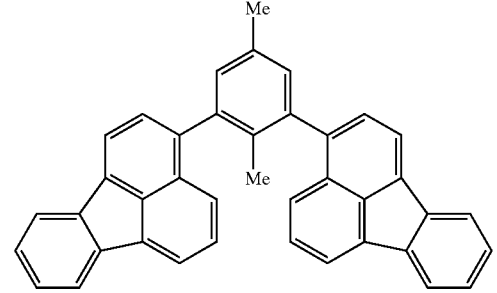
A-12
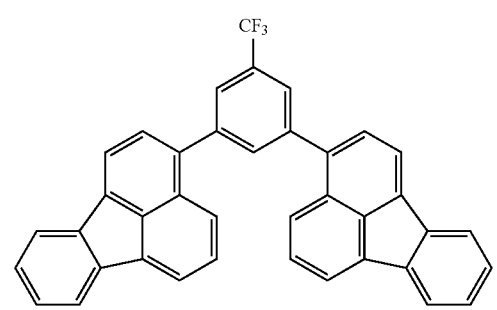
A-13
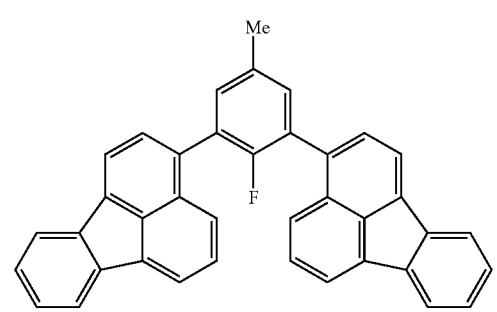
Compound group B
B-1
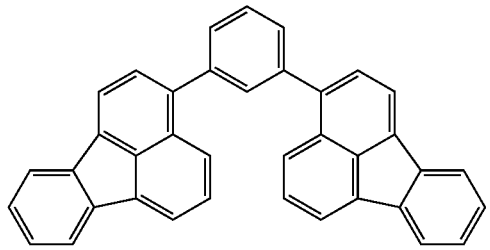
B-2
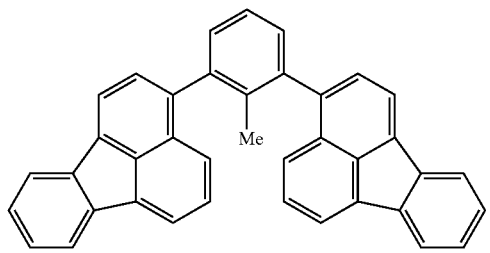
B-3
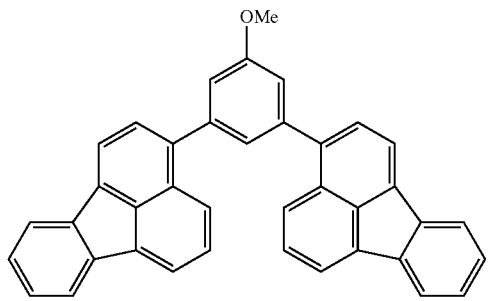
B-4
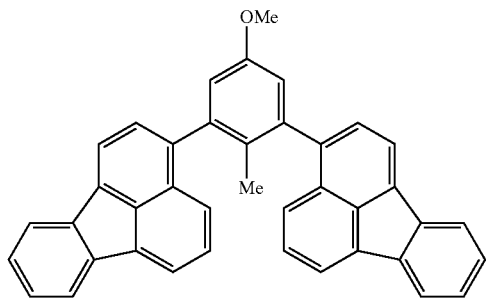
B-5
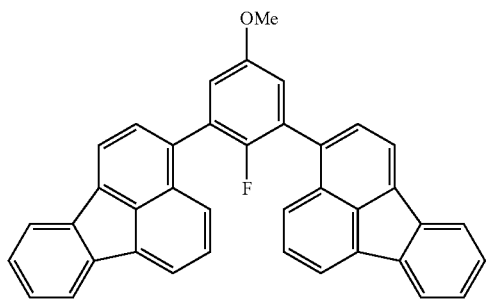

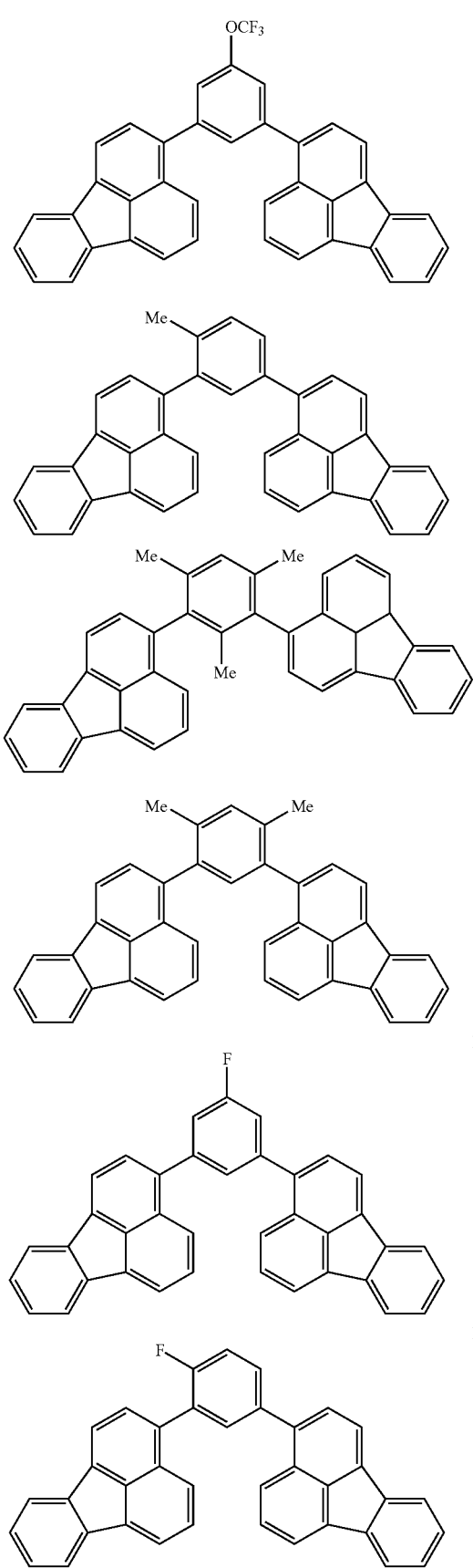

B-17
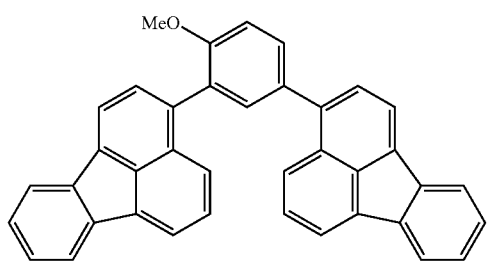

B-18
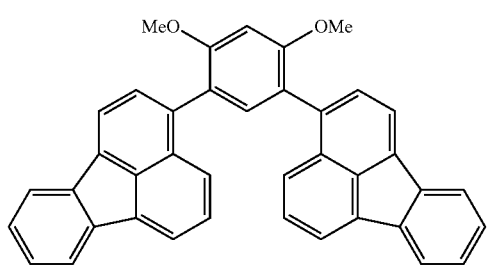

Compound group C

C-1
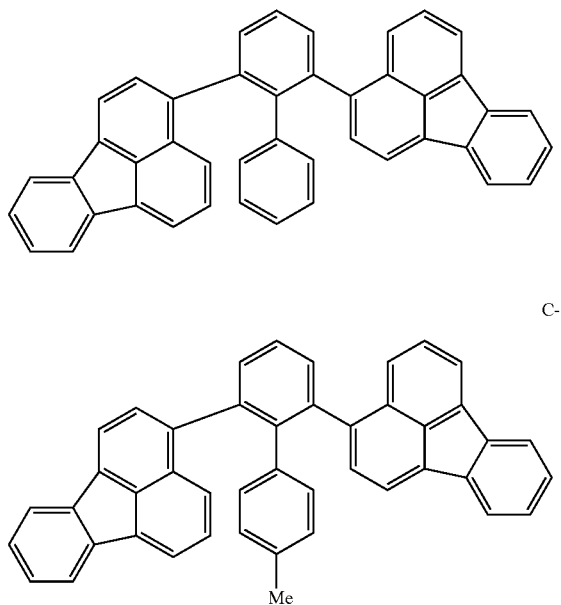

C-2

C-3

C-4
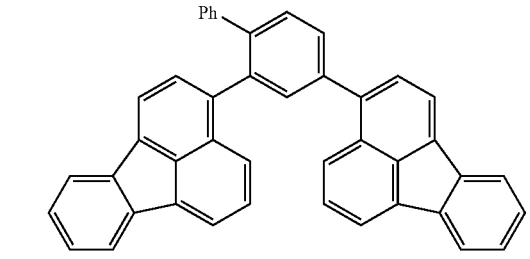

Compound group D

D-1
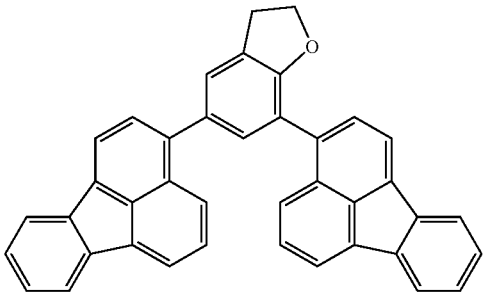

D-2
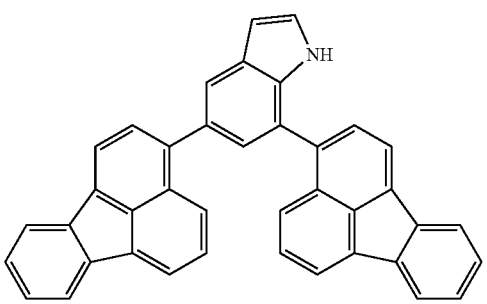

D-3
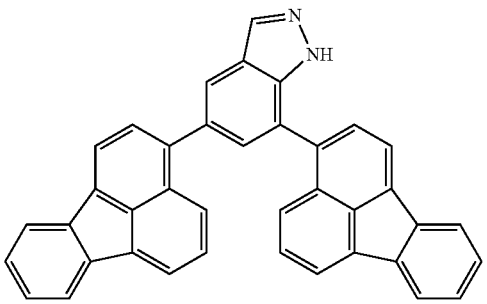

Of the above exemplified compounds, particularly in view of solubility, a compound in which at least one alkyl group is bonded to a benzene ring is more preferable. Some of such compounds are shown in compound group A and compound group B. These include, for example, compounds A-1 to A-13, B-2, B-4, and B-7 to B-9.

The compound of the present invention may be synthesized by using various methods.

For example, synthesis can be performed by a Suzuki-Miyaura coupling reaction between a pinacolborane compound derived from substituted or unsubstituted 3-bromofluoranthene and substituted or unsubstituted dibromobenzene.

In addition, instead of the pinacolborane compound, boronic acid may also be used. Formation of the pinacolborane compound can be performed, for example, by reaction between a halogen compound and 4,4,5,5-tetramethyl-[1,3, 2]dioxabororane in a toluene solution under the presence of [1,3-Bis(diphenylphosphino)propane]Nickel(II)dichloride as a catalyst.

Next, an organic light-emitting element of the present invention will be described in detail.

The organic light-emitting element of the present invention has an anode, a cathode, and an organic compound layer disposed between the above electrodes, and the organic compound layer includes the compound of the present invention.

The organic compound layer may include only the compound of the present invention.

The organic compound layer may be any one of a hole injection layer, a hole transport layer, an electron blocking layer, a light-emitting layer, a hole blocking layer, an electron transport layer, and an electron injection layer.

The compound of the present invention is preferably used in the light-emitting layer, the electron transport layer or the hole transport layer and is more preferably used in the light-emitting layer.

When one of the hole transport layer, the electron blocking layer, the hole blocking layer, the electron transport layer, and the electron injection layer emits light, the layer emitting light may be called a light-emitting layer.

The organic compound layer may be formed by a vacuum evaporation method or a solution coating method. The light-emitting layer may include a known low molecular weight-based or polymer-based hole transport compound, light-emitting compound, or electron transport compound in addition to the compound of the present invention.

The anode and the cathode may be optionally formed from preferable materials.

At least one of the electrodes may function as a light emission-side electrode.

The light emission-side electrode is a transparent or a semi-transparent electrode.

The organic light-emitting element of the present invention may further include a protection layer.

The organic light-emitting element of the present invention may further include a switching element controlling light emission and non-light emission. As the switching element, for example, a thin film transistor (TFT) may be mentioned.

The organic light-emitting element of the present invention may be either a top emission type in which light emission is not performed through a substrate supporting the organic light-emitting element or a bottom emission type in which light emission is performed through the substrate.

When the compound of the present invention is used as a guest material of the light-emitting layer of the organic light-emitting element according to the present invention, as a host material, a condensed ring hydrocarbon compound having at least four rings is preferable.

As this condensed ring hydrocarbon compound having at least four rings, for example, a pyrene compound, a fluoranthene compound, benzofluoranthene compound, a tetracene compound, a triphenylene compound, and a crysene compound may be mentioned.

As the pyrene compound among those mentioned above, for example, the following materials may be mentioned.

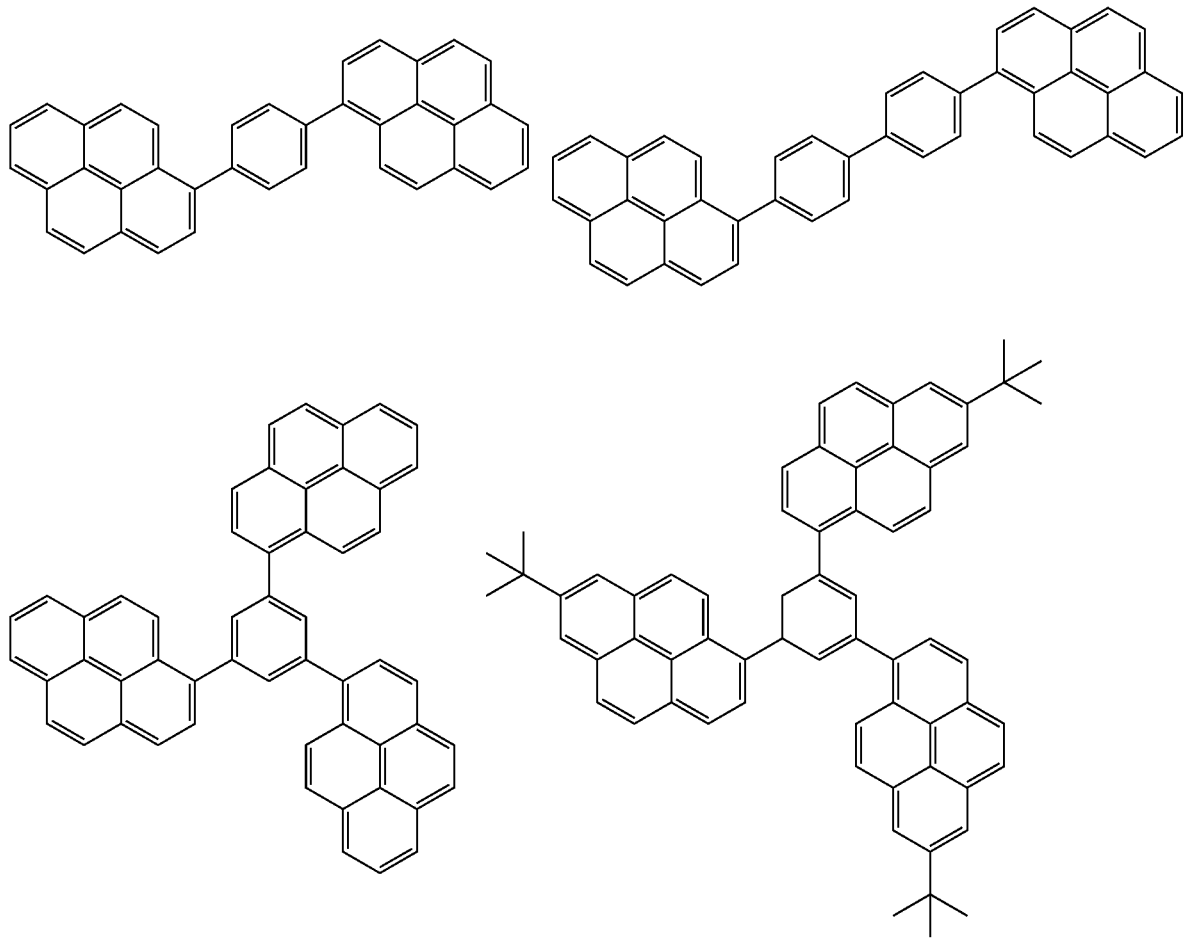

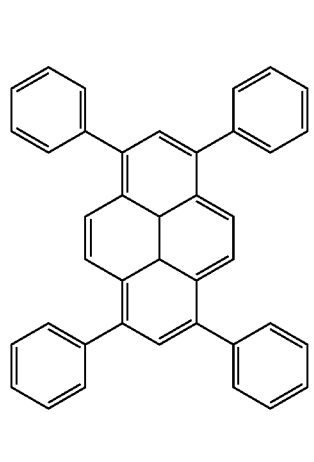
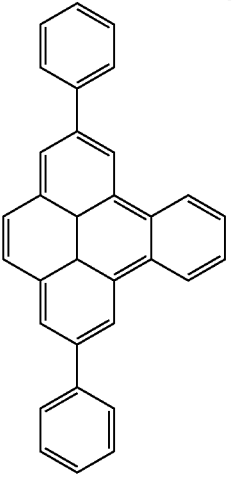
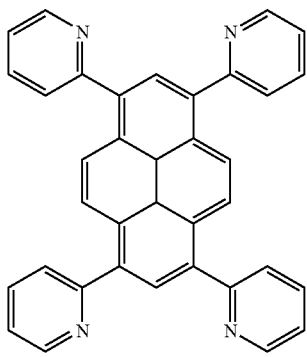
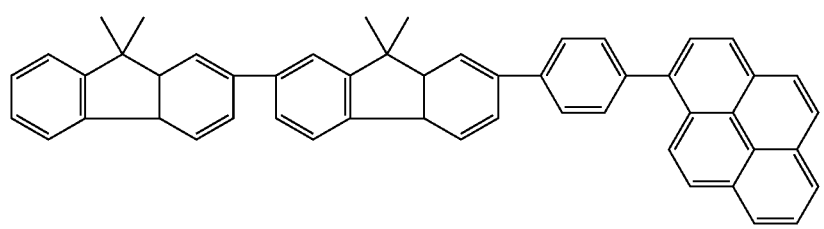
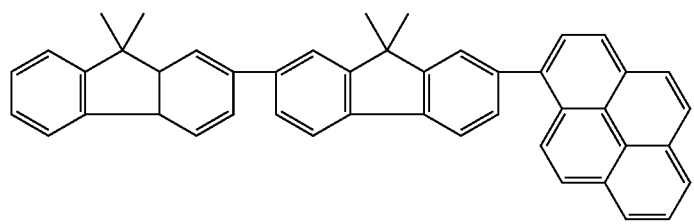
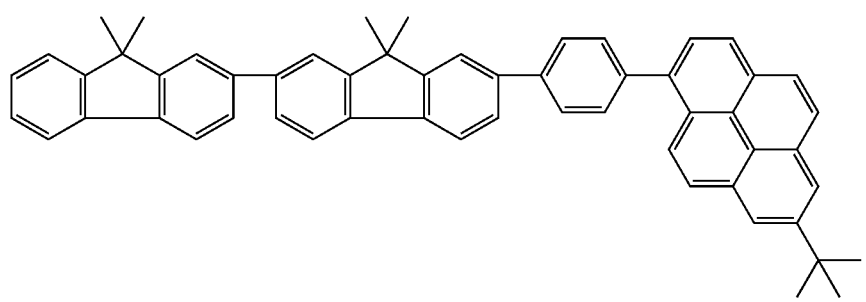
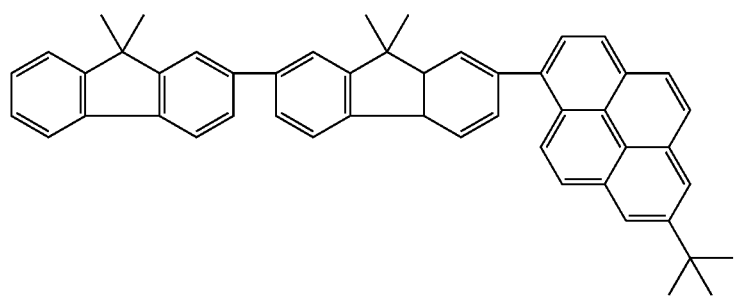

-continued

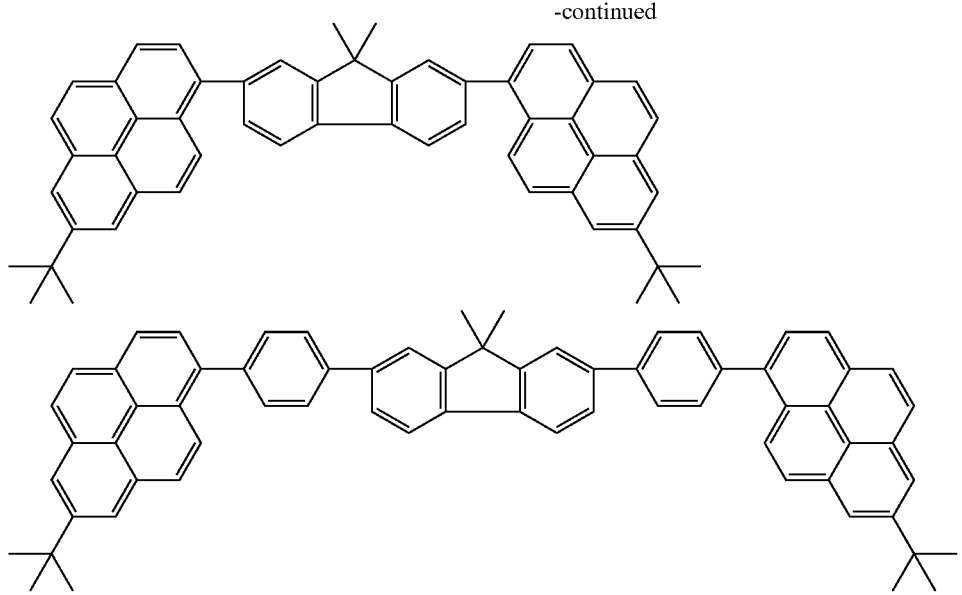

EXAMPLES

Hereinafter, the present invention will be described in detail with reference to the examples; however, the present invention is not limited thereto.

Example 1

Method for Manufacturing Exemplified Compound No. A-2

The exemplified compound A-2 of the present invention can be manufactured, for example, by the following method.

With reference to J. Am. Chem. Soc. (1991), 113, 4238, which is incorporated herein by reference, 3,5-dibromo-tert-butylbenzene was synthesized from 4-tert-butylaniline.

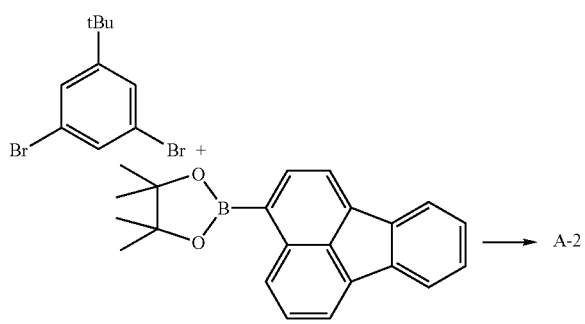

In a nitrogen atmosphere, 560 ml (1.93 mmole) of 1,3-dibromo-5-tert-butylbenzene, 1 g (4.06 mmole) of 2-(fluoranthene-3-yl)-4,4,5,5-tetramethyl-[1,3,2]dioxabororane were dissolved in a mixed solvent of toluene (100 ml) and ethanol (50 ml), and an aqueous solution containing 860 mg (8.12 mmole) of sodium carbonate and 15 ml of distilled water was added to the above mixture, followed by stirring at 50° C. for 30 minutes. Subsequently, tetraxis(triphenylphosphine)palladium (446 mg, 0.386 mmole) was added and the resulting mixture was then heated and stirred for 3 hours using a silicone oil bath heated to 90° C. After cooling the mixture to room temperature, and water, toluene, and ethyl acetate were then added, an organic layer was separated, a water layer was further extracted (twice) with a mixed solvent of toluene and ethyl acetate, and an organic layer thus obtained was added to the organic layer solution which was first separated. After the organic layer was washed with a saturated salt solution, drying was performed using sodium sulfate. The solvent was removed by distillation, and the residue was purified by silica gel column chromatography (toluene:heptane=1:3), followed by vacuum drying at 120° C. Furthermore, sublimation purification was performed, so that 620 mg of an exemplified compound in the form of a pale yellow solid was obtained.

By a matrix-assisted laser deposition ionization-time of flight type mass spectrometric (MALDI-TOF MA) analysis, a mass of 534.6, that was M of this compound, was confirmed (no matrix).

In addition, a $^1$H-NMR (CDCl$_3$) spectrum of the exemplified compound A-2 was measured. The results are shown in the FIGURE. The values shown in the vicinities of the individual peaks of the spectrum shown in the FIGURE each indicate the ratio of integral value (ratio of the number of protons) obtained when the peak at 1.50 ppm is regarded as 9. The regions and the respective ratios of integral values are as follows: 1.50 ppm, 9; 7.39 to 7.41 ppm, 3.93; 7.64 to 7.70 ppm, 3.27; 7.73 to 7.76 ppm, 4.19; 7.93 to 7.96 ppm, 4.14; 7.97 to 8.04 ppm, 4.34; and 8.06 to 8.08 ppm, 2.29. In addition, the peak of CHCl$_3$ is derived from a deuterium-hydrogen exchanged compound of the solvent (CDCl$_3$) used for the measurement.

When the glass transition temperature (Tg) of the compound in a glass state was measured starting at room temperature, by raising the temperature at the rate of 10° C./min by Perkin Elmer DSC (Pyrisl), the Tg was 121° C.

In addition, higher occupied molecular orbital (HOMO) energy was measured by photoelectron analysis (AC-1 manufactured by Rikenkiki Co., Ltd). Lowest unoccupied molecular orbital (LUMO) energy was obtained by a conventional calculation method using a measured energy gap value and the above HOMO energy. The HOMO energy was 5.98 eV, the energy gap was 3.04, and the LUMO energy was −2.94 eV by calculation.

Of the exemplified compounds having the structures shown above, synthesis methods of compounds other than the compound A-2 will be described.

[Synthesis of Exemplified Compound No. B-2]

The exemplified compound No. B-2 could be synthesized in a manner similar to that in Example 1 except that 2,6-dibromotoluene was used instead of 1,3-dibromo-5-tert-butylbenzene of Example 1.

[Synthesis of Exemplified Compound No. A-7]

The exemplified compound No. A-7 could be synthesized in a manner similar to that in Example 1 except that 1,5-dibromo-2,4,5,6-tetramethylbenzene was used instead of 1,3-dibromo-5-tert-butylbenzene of Example 1.

[Synthesis of Exemplified Compound No. A-12]

The exemplified compound No. A-12 could be synthesized in a manner similar to that in Example 1 except that 1,3-dibromo-5-trifluoromethylbenzene was used instead of 1,3-dibromo-5-tert-butylbenzene of Example 1.

[Synthesis of Exemplified Compound No. A-3]

The exemplified compound No. A-3 could be synthesized in a manner similar to that in Example 1 except that 2-(8-tert-butylfluoranthene-3-yl)-4,4,5,5-tetramethyl-[1,3,2]dioxabororane was used instead of 2-(fluoranthene-3-yl)-4,4,5,5-tetramethyl-[1,3,2]dioxabororane of Example 1.

Comparative Example 1

Comparative compound 1 was synthesized in a manner similar to that in Example 1 except that 1,4-dibromobenzene was used instead of 1,3-dibromo-5-tert-butylbenezene of Example 1.

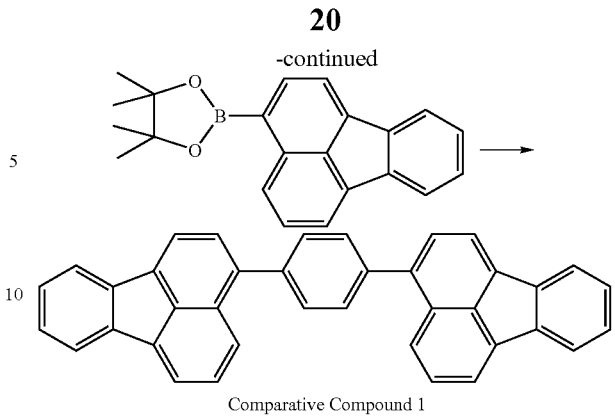

Comparative Compound 1

In a manner similar to that in Example 1 under conditions similar thereto, the HOMO energy, the energy gap, and the LUMO energy were measured and calculated. The HOMO energy was 5.97 eV, and the LUMO energy was 3.03 eV. The energy gap was 2.94, and compared to that of the exemplified compound A-2 of the present invention characterized in that the substitution was performed at the meta-position, the energy gap was narrow.

In addition, diluted toluene solutions of the exemplified compound A-2 and the comparative compound 1 at a concentration of $1\times10^{-5}$ mol/l were prepared, and emission spectra were measured by Hitachi spectrofluorometer F-4500. The PL spectrum of the comparative compound 1 had an emission wavelength of 460 nm and showed a red shift from a wavelength of 457 nm of the exemplified compound A-2.

Example 2

An organic light-emitting element was formed by the following method.

On a glass substrate used as a substrate, a film of indium tin oxide (ITO) having a thickness of 120 nm was formed as an anode by sputtering, so that a transparent conductive support substrate was prepared. The substrate thus formed was washed by ultrasonic waves sequentially using acetone and isopropyl alcohol (IPA) and was then washed by boiling IPA, followed by drying. Furthermore, after UV/ozone washing was performed, the transparent conductive support substrate was used.

As a hole transport material, a chloroform solution containing compound 1 having the following structure at a concentration of 0.2 percent by weight was prepared.

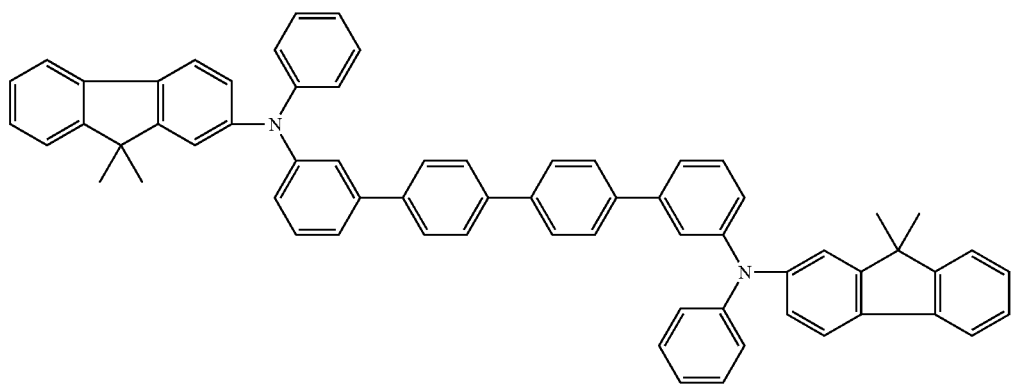

Compound 1

The solution thus prepared was dripped onto the ITO electrode, spin coating was performed by rotation thereof at 500 rpm for 10 seconds and then at 1,000 rpm for 1 minute, so that a film was formed. Subsequently, drying was performed at 80° C. for 10 minutes in a vacuum oven, so that the solvent in the film was totally removed. The thickness of a hole transport layer was 15 nm.

Next, on the hole transport layer, the exemplified compound No. A-2 as a first compound and compound 2 having the following structure as a second compound were co-deposited (co-deposition ratio of 5:95), so that a light-emitting layer having a thickness of 25 nm was formed. The deposition

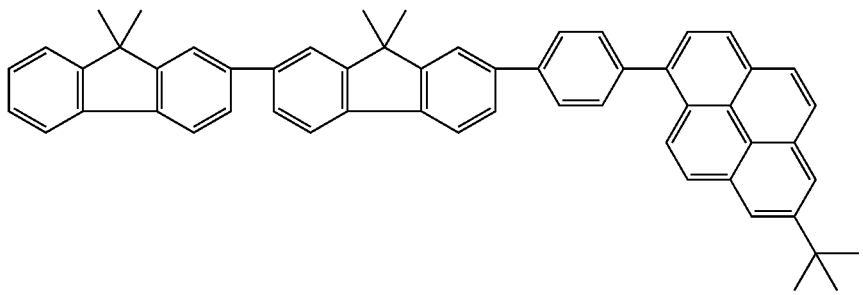

Compound 2 was performed at a degree of vacuum of $1.0 \times 10^{-4}$ Pa and a deposition rate in the range of 0.2 to 0.3 nm/sec.

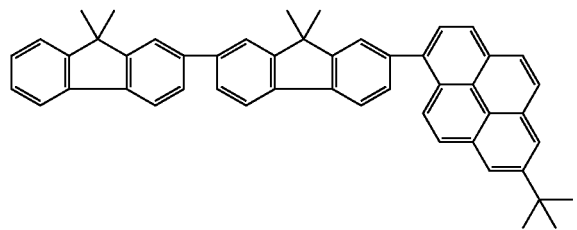

Furthermore, as an electron transport layer, a film having a thickness of 25 nm was formed by vacuum evaporation using 2,9-[2-(9,9'-dimethylfluorenyl)]-1,10-phenanthroline. The deposition was performed at a degree of vacuum of $1.0 \times 10^{-4}$ Pa and a deposition rate in the range of 0.2 to 0.3 nm/sec.

Next, a film having a thickness of 0.5 nm was formed on the above organic layer by vacuum evaporation using lithium fluoride (LiF), and in addition, an aluminum film having a thickness of 100 nm was formed as an electron injection electrode (cathode) by a vacuum evaporation method, so that the organic light-emitting element was formed. In the deposition, the degree of vacuum was set to $1.0 \times 10^{-4}$ Pa, the deposition rate of LiF was set to 0.05 nm/sec, and the deposition rate of aluminum was set in the range of from 1.0 to 1.2 nm/sec.

The organic EL element thus obtained was covered with a protective glass substrate in a dry atmosphere so as not to cause element degradation by moisture adsorption, and sealing with an acrylic resin-based adhesive was then performed.

By using the element thus obtained, when a voltage of 4 V was applied between the ITO electrode (anode) used as a positive electrode and the Al electrode (cathode) used as a negative electrode, blue light emission having an emission efficiency of 3.8 μm/W was observed. In addition, the CIE chromaticity was x=0.15 and y=0.17, and hence blue light emission was observed.

Furthermore, when a voltage was applied to this element for 100 hours in a nitrogen atmosphere, continuous light emission was stably observed.

Example 3

An element was formed in a manner similar to that of Example 2 except that the above exemplified compound No. A-2 as a first compound and compound 3 as a second compound were co-deposited at a ratio of 25:75.

Compound 3

When a voltage of 4V was applied to the element of this example, light emission having a light emission efficiency of 3.8 μm/W was observed. In addition, the CIE chromaticity was x=0.16 and y=0.22, and hence a blue light emission was observed.

Furthermore, when a voltage was applied to this element for 100 hours, continuous light emission was stably observed.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2006-119358 filed Apr. 24, 2006 and No. 2007-042664 filed Feb. 22, 2007, which are hereby incorporated by reference herein in their entirety.

What is claimed is:

1. A compound represented by general formula (1)

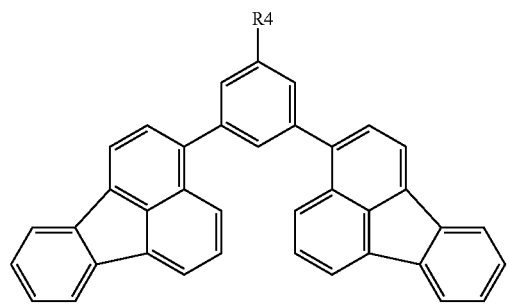

wherein R4 represents a substituted or an unsubstituted alkyl group.

2. The compound of claim 1, where in the compound is a blue light-emitting compound.

3. An organic light-emitting element comprising: an anode; a cathode; and at least one organic compound layer disposed between the anode and the cathode,
  wherein the organic compound layer comprises the compound according claim 1.

4. The organic light-emitting element according to claim 3, wherein the organic compound layer is a light-emitting layer.

5. The organic light-emitting element according to claim 4, wherein the light-emitting layer comprises a host material and a guest material which comprises the compound represented by general formula (1).

* * * * *